(12) United States Patent
Patankar

(10) Patent No.: US 9,259,441 B2
(45) Date of Patent: Feb. 16, 2016

(54) HERBAL COMPOSITION FOR THE TREATMENT OF KIDNEY STONE AND OTHER URINARY TRACT DISORDERS

(76) Inventor: Suresh Balkrishna Patankar, Pune (IN)

(*) Notice: Subject to any disclaimer, the term of this patent is extended or adjusted under 35 U.S.C. 154(b) by 0 days.

(21) Appl. No.: 14/002,940

(22) PCT Filed: Mar. 5, 2012

(86) PCT No.: PCT/IN2012/000155
§ 371 (c)(1),
(2), (4) Date: Sep. 3, 2013

(87) PCT Pub. No.: WO2012/127498
PCT Pub. Date: Sep. 27, 2012

(65) Prior Publication Data
US 2013/0337057 A1    Dec. 19, 2013

(30) Foreign Application Priority Data

Mar. 3, 2011 (IN) .......................... 601/MUM/2011

(51) Int. Cl.
*A61K 36/8998* (2006.01)
*A61K 36/21* (2006.01)
*A61K 36/88* (2006.01)
*A61K 36/185* (2006.01)
*A61K 35/22* (2015.01)

(52) U.S. Cl.
CPC .............. *A61K 35/22* (2013.01); *A61K 36/185* (2013.01); *A61K 36/21* (2013.01); *A61K 36/88* (2013.01); *A61K 36/8998* (2013.01)

(58) Field of Classification Search
None
See application file for complete search history.

(56) References Cited

U.S. PATENT DOCUMENTS 6,896,907 B2 * 5/2005 Khanuja et al. ............... 424/558

FOREIGN PATENT DOCUMENTS

IN    2128/MUM/2006    *  8/2008

OTHER PUBLICATIONS

Success Ayur online blog entry "Treatment for excess urine," Apr. 24, 2009; http://successayur.blogspot.com/2009/04/treatment-for-excess-urine.html.*
The Tribune online article by Vatsyayan "The stone-breaker" Jan. 23, 2002; http://www.tribuneindia.com/2002/20020123/health.htm#4.*
Ayurveda Sanjeevani online blog entry "Some hints to control kidney stones or stones related to urinary tract," Jan. 4, 2007; http://ayurvedasanjeevani.blogspot.com/2007/01/some-hints-to-control-kidney-stones-or.html.*
Natarajan et al. "Growth of some urinary crystals and studies on inhibitors and promoters. II. X-ray studies and inhibitory or promotery role of some substances," Crystal Research and Technology 32(4):553-559, 1997.*
"International Search Report for PCT/IN2012/000155 dated Sep. 20, 2012".
"SG Phytopharma: "Stonvil Capsules"", 2010, pp. 1-2, Retrieved from the Internet: URL: http://www.sgphyto.com/stonvil_capsules.html [viewed on Aug. 22, 2013].
"Vaidya Marla Bajra Bajracharya (Dr. Mane) of Kathmandu: Diseases of the Urinary Bladder", 2010 pp. 1-3, Retrieved from the Internet: URL: http://www.ayurvedainnepal.com/disease/diseases-of-the-urinary-bladder/ [viewed on Aug. 22, 2013].
Patankar, Suresh , "A Prospective Randomized, Controlled Study to Evaluate the Efficacy and Telerability of Ayrvedic Formulation Varuna and Banana Stem in the Management of Urinary Stones", The Journal of Alternative and Complementary Medicine, vol. 14, No. 10 2008.
Radhawa, Gurpreet K. , "Cow urine distillate as bioenhancer", Retrieved from the Internet: URL: http://www.jaim.in/text.asp?2010/1/4/240/74089 [viewed on Aug. 22, 2013], Abstract only.
Varalakshimi, et al., "Effect of Crataeva nurvala in experimental urolithiasis", Journal of Ethnopharmacology, vol. 28, No. 3, Mar. 1, 1990, 313-321.

* cited by examiner

Primary Examiner — David J Blanchard
Assistant Examiner — Alissa Prosser
(74) Attorney, Agent, or Firm — Kramer & Amado, P.C.

(57) ABSTRACT

Discloses a novel synergistic herbal composition comprising combination of therapeutically effective amount of Vrun bhavit, Kadalikshar, Apamargkshar, Yavkshar and optionally Gomutrakshar along with pharmaceutical acceptable additives, useful for the treatment of kidney stone and other urinary disorders like inflammation and urinary stent related problems.

13 Claims, No Drawings

HERBAL COMPOSITION FOR THE TREATMENT OF KIDNEY STONE AND OTHER URINARY TRACT DISORDERS

TECHNICAL FIELD OF THE INVENTION

The present invention relates to a novel synergistic herbal composition comprising combination of therapeutically effective amount of herbal constituents/ingredients extracted from bark of *Crataeva nurvala* (Varuna); stem, kand i.e. yam and root of *Musa sapientum* (Banana); five different plant parts i.e. flower, leaves, seed, root, fruits of *Achyranthes aspera* (Aghada); and seeds of *Hordeum vulgare* (Yav/Satu), along with pharmaceutical acceptable additives, useful for the treatment of kidney stone and other urinary tract disorders like inflammation and urinary stent related problems.

BACKGROUND OF THE INVENTION

Kidney stones (ureterolithiasis) result from stones or renal calculi in the ureter. The stones are solid concretions or calculi (crystal aggregations) formed in the kidneys from dissolved urinary minerals. Nephrolithiasis refers to the condition of having kidney stones. Urolithiasis refers to the condition of having calculi in the urinary tract (which also includes the kidneys), which may form or pass into the urinary bladder. Ureterolithiasis is the condition of having a calculus in the ureter, the tube connecting the kidneys and the bladder.

Kidney stones typically leave the body by passage in the urine stream, and many stones are formed and passed without causing symptoms. If stones grow to sufficient size before passage on the order of at least 2-3 millimeters they can cause obstruction of the ureter. The resulting obstruction causes dilation or stretching of the upper ureter and renal pelvis as well as muscle spasm of the ureter, trying to move the stone. This leads to pain, most commonly felt in the flank, lower abdomen and groin. Renal colic can be associated with nausea and vomiting. There can be blood in the urine, visible with the naked eye or under the microscope due to damage to the lining of the urinary tract.

There are several types of kidney stones based on the type of crystals of which they consist. The majority are calcium oxalate stones, followed by calcium phosphate stones. More rarely, struvite stones are produced by urea-splitting bacteria in people with urinary tract infections, and people with certain metabolic abnormalities may produce uric acid stones or cystine stones.

Many medicinal plants have been found useful in urinary disorders. Medicinal plants leads to find therapeutically useful compounds, thus more efforts should be made towards isolation and characterization of the active principles and elucidation of the relationship between structure and activity. The combination of traditional and modem knowledge can produce better drugs for kidney stones.

*Crataeva nurvala* is known in Indian medicine as Varuna. It is a small tree which grows wild along river banks throughout the Indian subcontinent, where it is also widely cultivated. The stem and root bark of this plant are the parts most often used medicinally. Crataeva has been used for centuries in eastern herbal traditions to treat a variety of health disorders. It is especially valued for its therapeutic effect on the urinary organs.

*Musa sapientum* also known in Indian medicine as Kadali (Banana tree), a native of South East Asia and Australia and which belong to the family musaceae, is a food crop grown in towns and villages in Nigeria. The tropical herb, has been traditionally used as a dietary food against intestinal disorders because of its soft texture and blandness. Every part of this tree has a lot of medicinal values. It helps to promote the retention of calcium, phosphorus and nitrogen which are essential in building up sound and regenerated tissues.

*Achyranthes aspera* is known in Indian medicine as Apamarg/Aghada. It is a species of plant in the Amaranthaceae family. It is distributed throughout the tropical world. It can be found in many places growing as an introduced species and a common weed. It is an invasive species in some areas, including many Pacific Islands environments.

Barley is a cereal grain derived from the annual grass *Hordeum vulgare*. Barley has many uses. It serves as a major animal fodder, as base malt for beer and certain distilled beverages, and as a component of various health foods. It is used in soups and stews, and in barley bread of various cultures.

*Hordeurn vulgare* is known in Indian medicine as Yav/Satu and has medicinal properties for curing kapha, pitta, cough, asthma, urinary retention, urinary tract infection, gastric ulcers, burns, headache, anemia and general debility. It is a good diet in convalescent period.

The herbal preparations for the treatment of kidney stone have been known since long for its safety. Some herbs useful for the treatment of kidney stone are *Petroselinum crispum* (Parsley), *Urtica dioica* (Nettle), *Taraxacum offcinale* (Dandelions), *Populus nigra* (poplar), *Betula alba* (birch), *Arctostaphylos uva-ursi* (bearberry), Menthe (mint), *Oryza sativa* (Rice), Marshmallow (*Althaea officinalis*), *Curcuma longa* (turmeric), Corn (*Zea mays*).

Further, the herbal preparations remove the kidney stones fast and more effectively without damaging the kidneys. These preparations are cost effective and having lesser side effects than allopathic medicines.

The applicant has disclosed a herbal formulation of a homogenized powdered mixture of extract prepared from bark of a plant selected from *Crataeva nurvala* and *Crataeva magna*; and extract prepared from stem of a plant selected from *Musa paradisiaca* L and *Musa sapientum* L; along with ash salt of banana root and pharmaceutical acceptable carrier, for the treatment of renal calculi, in his earlier Patent Application No. 2128/MUM/2006.

The applicants still felt a need to improve upon the earlier known herbal composition to achieve enhanced efficacy with more synergic effect and better patient compliance and which is cost effective for the treatment of kidney stone and other urinary disorders like inflammation and urinary stent related problems.

OBJECT OF THE INVENTION

Thus, an object of the present invention is to develop an improved novel synergistic herbal composition comprising combination of therapeutically effective amount of herbal constituents/ingredients extracted from *Crataeva nurvala* (Varuna), *Musa sapientum* (Banana), *Achyranthes aspera* (Aghada) and *Hordeum vulgare* (Yav/Satu), useful for the treatment of kidney stone and other urinary disorders like inflammation and urinary stent related problems.

Another object of the present invention is to provide an improved synergistic herbal composition for the treatment of kidney stones, post lithotripsy fragment stones, pre-operative treatment and expulsion of renal calculi, recurrence and reinformation of renal calculi, urinary disorders like inflammation and stent dysuria, with enhanced efficacy.

SUMMARY OF THE INVENTION

In accordance with the above, the present invention discloses a novel synergistic herbal composition comprising combination of therapeutically effective amount of herbal constituents/ingredients extracted from bark of *Crataeva nurvala* (Varuna); stem, kand i.e yam and root of *Musa sapientum* (Banana); five different parts i.e. flowers, leaves, seed, root, fruits of *Achyranthes aspera* (Aghada) and seeds of *Hordeum vulgare* (Yav/Satu), in combination with pharmaceutical acceptable additives, useful for the treatment of kidney stone and other urinary disorders like inflammation and urinary stent related problems.

In another aspect, the present invention provides a process for preparation of said herbal composition.

DETAILED DESCRIPTION OF THE INVENTION

The invention will now be described in detail in connection with certain preferred and optional embodiments, so that various aspects thereof may be more fully understood and appreciated.

For the purpose of this invention, the definitions of terms are as follows:—

Bhavit: implies to improve concentration with repetition of same procedure.
Churna: implies to fine powdered plant/plants used as internal (used as medicine with water or in food) and external (application, snuff) medicine
Kadha: implies concentrated water extracts
Swaras: implies to fresh juice of herbs
Bhavna: implies to the procedure where medicinal ingredients (most probably heavy metals and minerals but occasionally herbs and entire formulations) are pre-treated or processed with specific liquid preparation to purify/detoxify them or manipulate their potency.
Bharad: implies to crude powder of plants material.
Kshar: implies to ashes of plant drugs or the derivatives of such ashes in the form of solution or crystals
Gomutra: Cow urine
Ghee: A class of clarified butter that originated in South Asia and is commonly used in South Asian (Indian, Bangladeshi, Nepali and Pakistani) cuisine.
Herbmed: Combination of Varun and Banana extracts
Herbmed Plus: Combination of extracts of Varun bhavit kadali swaras bhavit; Kadalikshar; Apamargkshar; Yavkshar and optionally with Gomutrakshar.

Preparation of Herbal Composition:

For the preparation of composition initially raw material used were authenticated at Agharkar Research Institute Pune, Maharashtra, India, having internationally recognized Agharkar Herbarium at Maharashtra Association for Cultivation of Science.

The kshar required for the preparation of herbmed plus viz. Kadalikshar; Apamargkshar; Yavkshar were prepared from above authenticated material at Vishvarang Ayurved Pharmacy Pune Maharashtra, India, which is Food and Drug Administration approved by Maharashtra state of India using Ayurvedic Pharmacopeia protocol.

In a preferred embodiment, the present invention provides a novel synergistic herbal composition comprising combination of therapeutically effective amount of herbal constituents/ingredients extracted from bark of *Crataeva nurvala* (Varuna); stem, kand i.e. yam and root of *Musa sapientum* (Banana); five different parts i.e. flower, leaves, seed, root, fruits of *Achyranthes aspera* (Aghada) and seeds of *Hordeum vulgare* (Yav/Satu), along with pharmaceutical acceptable additives, useful for the treatment of kidney stone and other urinary disorders like inflammation and urinary stent related problems.

The extract from the bark of *Crataeva nurvala* (Indian name: Varuna) is herein referred as "Varun bhavit" throughout the specification.

The extract from stem, yam and root of *Musa sapientum* (Indian name: Kadali/Banana) is herein referred as "Kadalikshar" throughout the specification.

The extract from the five different parts i.e. flowers, leaves, seeds, roots, fruits of *Achyranthes aspera* (Indian name: Apamarg/Aghada) is herein referred as "Apamargkshar" throughout the specification.

The extract from seeds of *Hordeum vulgare* (Indian name: Yav/Satu) is herein referred as "Yavkshar" throughout the specification.

"Gomutrakshar", a Sanskrit word, as described herein throughout the specification refers to filtered, boiled, evaporated cow urine extract.

In another preferred embodiment, the present invention provides a novel synergistic herbal composition comprising combination of therapeutically effective amount of,
 a) Varun bhavit in an amount of about 15-85%;
 b) Kadalikshar in an amount of about 15-85%;
 c) Apamargkshar in an amount of about 15-85%; and
 d) Yavkshar in an amount of about 15-85% of the total composition along with pharmaceutical acceptable additives.

In another embodiment, the present invention provides a novel synergistic herbal composition comprising combination of therapeutically effective amount of,
 a) Varun bhavit in an amount of 50%;
 b) Kadalikshar in an amount of 15%;
 c) Apamargkshar in an amount of 15% and
 d) Yavkshar in an amount of 20% of the total composition along with pharmaceutical acceptable additives.

The novel synergistic herbal composition of the present invention further optionally comprises Gomutrakshar which is present in an amount of 15-85%; preferably 60%.

In another embodiment, the present invention provides a novel synergistic herbal composition comprising combination of therapeutically effective amount of,
 a) Varun bhavit in an amount of about 15-85%;
 b) Kadalikshar in an amount of about 15-85%;
 c) Apamargkshar in an amount of about 15-85%;
 d) Yavkshar in an amount of about 15-85%; and
 e) Gomutrakshar is present in an amount of 15-85% of the total composition along with pharmaceutical acceptable additives.

In another embodiment, the present invention provides a novel synergistic herbal composition comprising combination of therapeutically effective amount of,
 a) Varun bhavit in an amount of about 50%;
 b) Kadalikshar in an amount of about 15%;
 c) Apamargkshar in an amount of about 15%;
 d) Yavkshar in an amount of about 20% and
 e) Gomutrakshar is present in an amount of 60% of the total composition along with pharmaceutical acceptable additives.

In another embodiment, the present invention provides a novel synergistic herbal composition is suitable for oral, nasal, topical (including buccal and sublingual), vaginal or parenteral (including subcutaneous, intramuscular, intravenous, intradermal, intrathecal, intraocular and epidural) and rectal administration and also in other pharmaceutically accepted drug delivery systems.

In another embodiment, the present invention provides a novel synergistic herbal composition suitable for oral administration may be presented as discrete units such as capsules, cachets or tablets each containing a predetermined amount of active ingredient; as powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste or in other pharmaceutically accepted form.

In another embodiment, the present invention provides a novel synergistic herbal composition particularly in the form of a tablet or capsule.

The recommended dose of herbal composition of the present invention is 500 mg capsule twice a day.

In another embodiment, the present invention provides a novel synergistic herbal composition for the treatment of kidney stones, post lithotripsy fragment stones, pre-operative treatment and expulsion of renal calculi, recurrence and reformation of renal calculi, urinary disorders like inflammation and stent dysuria, with enhanced efficacy.

In another preferred embodiment, the invention provides process for preparation of herbal constituents used according to the invention comprises the following steps:—

1. Preparation of Varun Bhavit Kadali Swaras Bhavit:—
  i. The Barks obtained from *Crataeva nurvala* (Varun) (1 part) are grounded to get a powdered '(Bharad) Mass'. 0.5 part of it grounded so fine to get fine powder of varun called 'Varun Churna'.
  ii. Water is added to the 'Varun Bharad Powder mass' in the ratio of 1:16. This watery mixture is boiled to reduce it to 1:8 for approx. 5 to 6 hrs time, to obtained 'Kadha'.
  iii. Kadha obtained in step (ii) is added in the Varun churna of step (i) and this mixture is kneaded and dried and pulverized to obtain a 'Homogenized powdered' mixture of Varun Churna and Varun Kadha. [This called as one bhavana for which approximately 5 to 6 hrs. are required]
  iv. Above step (iii) is repeated for seven times and the product obtained is kept in oven up to 35 to 40° C. and dried to obtain 'Varun Bhavit'.
  v. Stem of *Musa paradisiaca* L./*Musa sapientum* L. (1 part) are chopped into smaller pieces and are grounded in mixer. The grounded material is filtered to obtain jelly like aqueous extract called 'Kadali Swaras'.
  vi. Varun Bhavit Powder as obtained in step (iv) is added in Kadali Swaras of step (v) in proportion of 1:3.2 so that the powder is fully dissolved in the Kadali Swaras. The said mixture is kneaded & dried and pulverized further to obtain a homogenized powdered mixture of 'Varun Bhavit and Kadali Swaras'. [This called as one bhavana for which approximately 5 to 6 hrs. are required]
  vii. Above step (vi) is repeated for seven times and the product obtained is kept in oven up to 35 to 40° C. and dried to obtain the fine powder of 'Varun Bhavit Kadali Swaras Bhavit'.
2. Preparation of Banana Kshar:—
  i. Banana stem, root and kand i.e. yam are dried (1 part) in sunlight to obtain dried mass. These dried banana stems are burnt to obtained an ash.
  ii. This ash is added in the water.
  iii. The contents are stirred to obtain a suspension. This Suspension is allowed to settle. The excess water is decanted.
  iv. The residual ash was discarded.
  v. The decanted water is boiled and is allowed to evaporate completely to obtain Banana kshar or Kadali kshar.
3. Preparation of Apamarg (Aghada) Kshar:—
  i. Total plant of Apamarg (Aghada) consisting of flower, leaves, seed, root, fruits (one part) is well dried in sunlight to obtain a dry form. These five parts are burnt to obtain a white ash.
  ii. This ash is then filtered and is added in water and contents are stirred to obtain a suspension.
  iii. This suspension is then allowed to settle. The excess water is decanted.
  iv. The residual ash was discarded.
  v. The decanted water is boiled & is allowed to evaporate completely to obtain Apamarga kshar.
4. Preparation of Yav Kshar:—
  i. Yav grains are mixed with Ghee in 1: 0.004 proportion (for eg. 1 kg of Yav with 4 gm of ghee) and burn in the iron container to obtain a white ash.
  ii. This ash is allowed to cool in open space (Normal Temp).
  iii. After cooling this ash is added in the water & contents are stirred to obtain a suspension.
  iv. This suspension is then allowed to settle. The excess water is decanted.
  v. The residual ash is discarded.
  vi. The decanted water is boiled and is allowed to evaporate completely to obtain Yavkshar.

All the above four constituents i.e. Varun bhavit kadali swaras bhavit, Kadali kshar, Apamarg kshar, and Yav kshar are mixed together and formulated in the form of capsule, for the treatment of kidney stone and other urinary disorders like inflammation and urinary stent related problems.

Preparation of Above Invention in the Form of Capsule

Formulation of the present invention suitable for oral administration may be presented as discrete units such as capsule, provided herein below is typical formulation of a unit dosage form in the form of a capsule.

| | |
|---|---|
| Combination of Vrun bhavit kadali swaras bhavit | 250 mg |
| Kadali kshar | 75 mg |
| Apamarg kshar | 75 mg |
| Yav kshar | 100 mg |

The ingredients were filled in a pharmaceutical acceptable capsule. Typically the therapeutically effective dose of the unit dosage from is 500 mg of the finished unit dosage form two times a day in case of adult's patients.

In another embodiment, Gomutrakshar is optionally given together with the above formulation, wherein Gomutrakshar is prepared by following steps:—
  i. First filtering the cow's urine.
  ii. Then filtered urine is boiled and allowed to evaporate completely to obtain Kshar of cow's urine.

The therapeutically effective dose in the form of capsule of Herbmed plus 500 mg with Gomutrakshar 150 mg given together for twice a day.

The herbal composition of the present invention is suitable for both humans as well as veterinary use, consists of a synergistic combination of aforesaid herb extracts together with one or more acceptable carriers and optionally ingredients. The carriers must be acceptable in the sense of being compatible with the other ingredients of the formulation and not deleterious to the recipient thereof.

In an embodiment, the present invention provides a method of treating a subject i.e. human suffering from kidney stone and other urinary disorders like inflammation and urinary stent related problems, comprising administering a novel synergistic herbal composition comprising Varun bhavit kadali swaras bhavit; Kadalikshar; Apamargkshar; Yavkshar and optionally comprising Gomutrakshar along with pharmaceutical acceptable additives.

In an another embodiment, the present invention provides a method of treating a subject suffering from kidney stones, post lithotripsy fragment stones, pre-operative treatment and expulsion of renal calculi, recurrence and reformation of renal calculi, urinary disorders like inflammation and stent dysuria, comprising administering a novel synergistic herbal composition comprising Varun bhavit kadali swaras bhavit; Kadalikshar; Apamargkshar; Yavkshar and optionally comprising Gomutrakshar along with pharmaceutical acceptable additives.

In an another embodiment, the present invention provides a method of treating a subject i.e. human suffering from kidney stone and other urinary disorders like inflammation and urinary stent related problems, comprising administering a novel synergistic herbal composition of the present invention which is in the form of capsules, cachets, tablets, powder, suspension, emulsion or paste or in other pharmaceutically accepted form.

In another embodiment, the present invention provides a method of treating a subject suffering from kidney stone and other urinary disorders like inflammation and urinary stent related problems by administering a novel synergistic herbal composition of the present invention through oral, nasal, topical (including buccal and sublingual), vaginal or parenteral (including subcutaneous, intramuscular, intravenous, intradermal, intrathecal, intraocular and epidural) and rectal administration and also in other pharmaceutically accepted drug delivery systems.

In yet another embodiment, the present invention provides use of a novel synergistic herbal composition of the present invention for the treatment of kidney stone and other urinary disorders like inflammation and urinary stent related problems.

All the ingredients of the herbal composition of the present invention are well standardized with acceptable impurity profiles. All the ingredients were reported to be safe in literature. Further, the product of the present invention has been proven to be safe. The safety and clinical efficacy of the composition is proved on humans with effective removal of kidney stones and urinary disorders like inflammation and stent related problems.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Preparation of Varun Bhavit:— i. The Barks obtained from *Crataeva nurvala* (Varun) (1 part) are grounded to get a powdered '(Bharad) Mass'. Some part of it grounded so fine to get fine powder of varun called Varun Churna.
ii. Water is added to the Varun Bharad Powder mass in the ratio of 1:16. This watery mixture is boiled to reduce it to 1:8 for approx. 5 to 6 hrs time to obtained Kadha.
iii. Kadha obtained in step (ii) is added in the Varun churn of step (i) and this mixture is kneaded and dried and pulverized to obtain a 'Homogenized powdered' mixture of Varun Churna and Varun Kadha. [This called as one bhavna for which approximately 5 to 6 hrs are required]
iv. Above step (iii) is repeated for seven times and the product obtained is kept in oven up to 35 to 40° C. and dried to obtain Varun Bhavit.
v. Stem of *Musa paradisiaca* L./*Musa sapientum* L. (1 part) are chopped into smaller pieces and are grounded in mixer. The grounded material is filtered to obtain jelly like aqueous extract called Kadali Swaras.
vi. Varun Bhavit Powder as obtained in step (iv) is added in Kadali Swaras of step (v) in proper proportion of 1:3.2 so that the powder is fully dissolved in the Kadali Swaras. The said mixture is kneaded & dried and pulverized further to obtain a homogenized powdered mixture of Varun Bhavit and Kadali Swaras. [This called as one bhavna for which approximately 5 to 6 hrs are required]
vii. Above step (vi) is repeated for seven times and the product obtained is kept in oven up to 35 to 40° C. and dried to obtain the fine powder of Varun Bhavit Kadali Swaras Bhavit.

Example 2

Preparation of Banana Kshar:— i. Banana stem, root and kand i.e. yam are dried (1 part) in sunlight to obtain dried mass. These dried banana stems are burnt to obtained an ash.
ii. This ash is added in the water.
iii. The contents are stirred to obtain a suspension. This Suspension is allowed to settle. The excess water is decanted.
iv. The residual ash was discarded.
v. The decanted water is boiled and is allowed to evaporate completely to obtain Banana kshar or Kadali kshar.

Example 3

Preparation of Apamarg (Aghada) Kshar:— i. Total plant of Apamarg (Aghada) consisting of flower, leaves, seed, root, fruits (1 part) is well dried in sunlight to obtain a dry form. These five parts are burnt to obtain a white ash.
ii. This ash is then filtered and is added in water and contents are stirred to obtain a suspension.
iii. This suspension is then allowed to settle. The excess water is decanted.
iv. The residual ash was discarded.
vi. The decanted water is boiled & is allowed to evaporate completely to obtain Apamarga kshar.

Example 4

Preparation of Yav Kshar:— i. Yav grains are mixed with Ghee in 1: 0.004 proportion (for eg. 1 kg of Yav with 4 gm of ghee) and burn in the iron container to obtain a white ash.
ii. This ash is allowed to cool in open space (Normal Temp).
iii. After cooling this ash is added in the water & contents are stirred to obtain a suspension.
iv. This suspension is then allowed to settle. The excess water is decanted.
v. The residual ash is discarded.
vi. The decanted water is boiled and is allowed to evaporate completely to obtain Yavkshar.

Example 5

Preparation of Gomutrakshar:— i. First filtering the cow's urine.
ii. Then filtered urine is boiled and allowed to evaporate completely to obtain Kshar of cow's urine.

Example 6

Preparation of a Unit Dosage Form Capsule:—

| Combination of Vrun bhavit kadali bhavit | 250 mg |
| Kadali Kshar | 75 mg |
| Apamarg Kshar | 75 mg |
| Yav Kshar | 100 mg |

The ingredients were filled in a pharmaceutical acceptable capsule.

Example 7

| Sr. No. | Ingredients | Range |
| --- | --- | --- |
| 1. | Varun bhavit | 15-85% |
| 2. | Kadalikshar | 15-85% |
| 3. | Apamargkshar | 15-85% |
| 4. | Yavkshar | 15-85% |

Example 8

| Sr. No. | Ingredients | Range |
| --- | --- | --- |
| 1. | Varun bhavit | 15-85% |
| 2. | Kadalikshar | 15-85% |
| 3. | Apamargkshar | 15-85% |
| 4. | Yavkshar | 15-85% |
| 5. | Gomutrakshar | 15-85% |

Clinical Studies:
Efficacy of Herbmed Plus Using Laboratory Animals

Efficacy of Herbmed Plus was evaluated using Ethylene glycol induced Urolithiasis activity in Albino Rats. The ethylene glycol was given 0.75% through drinking water for 28 days and ensures urolithiasis after urine examination. These animals were treated with Herbmed plus 1000 mg/kg for 24 days and urine analysis as well as various biochemical parameters were studied. It was observed that there was significant reduction in number of oxalate crystals, total Protein, Uric acid, Calcium, Phosphorous, Magnesium, Sodium, Potassium levels. The enzyme profiles for liver and kidney were significantly altered. Indicating safety as well as efficacy of Herbmed Plus. The histological study of liver and kidney was also carried out to study safety and efficacy profiles in these animals.

Preclinical Safety Profiles of Herbmed Plus Formulations

1. Acute Oral Toxicity Study—

The acute oral toxicity of Herbmed Plus was evaluated by employing OECD guidelines Number 423, adopted on 17 Dec. 2001 using Albino Mice. This study was carried out by the oral route following the method of Litchfield & wilcoxon (1949) was found to be in GHS Category 5,>2000-5000 mg/kg body weight, with a LD50 cut off greater than 2000 mg/kg body weight and observing for 14 days for general health, behavioral changes and mortality. All animals were normal without any effect on health, behavior with no mortality indicating the oral LD50 was found to be greater than 2000 mg/kg it can be concluded that the Herbmed plus is safe for use.

2. Sub-Acute Toxicity Test—

The Sub-acute toxicity test of Herbmed plus was evaluated by following the FDA guidelines, following good laboratory practice regulations. The study was conducted to establish the toxicity of the test material also to study the toxic effect of the drug in albino rats with onset severity at 90 mg/kg, 180 mg/kg, 450 mg/kg administered by the oral route continuously for 90 days. All the animals appeared normal and showed no mortality and clinical signs till the end of the study, there was no statistically significant change in the body weight in all the study groups when compared with the control group animals. There was no significant difference in the food consumption and body weigh changes in animals. The animals were normal without any change in their behavioral pattern and there was no mortality. There was no difference in various blood parameters like Hb, PCV, RBC, WBC, PT, differential count, Plasma glucose, BUN, Total proteins, SAP, SGPT, urine parameters like Sp.gr., pH, Protein, Glucose, Ketones (Qualitative), microscopy parameters like PC, RBC, EC, Cr, Cast in comparison to control animals. There was no statistically significant change in the absolute and relative weights of the vital organs. There was no difference in gross necropsy and histology of heart, testis, ovaries, kidneys, Liver, Spleen, Lungs, Adrenals. Thus, indicating safety of Herbmed plus orally up to the dose of 450 mg/kg for 90 days.
Clinical Studies I;

A double blind two arm randomized clinical study was carried by AMAI Trust ACE Hospital, Pune, Maharashtra, India. The patient population had undergone for ESWL (Extracorporeal shockwave lithotripsy) treatment.

303 patients with severe symptoms and some complained of blood in the urine or sudden pain were asked to scan the urinary system using X-ray, Sonography and CT-Scan image. Patients with Kidney stones <2 cm were included in the trial.

Out of 303 patients 162 pts completed the trial and 141 patients were lost to follow up. Among 162 patients there were 39 Females and 123 Male patients. The average age of the patient was 11-60 years. They were randomly assigned both drugs. Patients were not allowed to take any other treatment during the trial and only if the pain was severe they were given standard therapy and were recorded. Treatment was given for 12 weeks or till the stone clearance. Efficacy was evaluated on the basis of CT-scan, sonographic image of the calculi and Pain index to confirm the stone clearance. The sonographic/CT-Scan images were obtained at the start, during and after the treatment. Successful clearance is defined as stone free patients or patients without any symptoms and having fragments <3 mm in size.

Method 303 patients included in the trial had Kidney stone of size <2 cm. All the patients were given lithotripsy (ESWL) treatment. After the treatment, they were divided in two groups and given the drugs. In addition patients were also instructed about the diet and fluid intake so that this factor remains uniform in both the groups. Patients were requested to record pain experienced during passage of stone on a visual analogue scale. 162 patients participated in the studies.

Group 1—(Herbmed)

There were 54 patients in group-1 these patients were administered HERBMED in the form of capsule 500 mg which contains Varun extract and banana kshar 250 mg each.

Group 2—(Herbmed Plus)

There were 108 patients in group-2 these patients were administered HERBMED PLUS in the form of capsule of 500 mg which contains Varun extract, Banana kshar, Yav kshar, Aghada kshar in proportion of 50%, 15%, 20%, 15% respectively, along with Gomutrakshar 300 mg.

Results
Litho Trial

After giving lithotripsy to renal/ureteric stone, patient was included in the trial who has good fragmentation on lithotripsy. One group was given Herbmed Plus and another group was given Herbmed for the maximum period of 3 months. Total 303 patients were included in the trial, 141 pts were lost to follow up. Out of total completed follow up of 162 pts, 108 pts were in group Herbmed Plus, 54 were in Herbmed group.

Complete clearance was noted in 98 patients in Herbmed Plus group (90.7%) and completed clearance in Herbmed was in 31 patients (57.4%). Average duration of clearance in Herbmed Plus group was 8.7 weeks and in Herbmed group 10.4 weeks. Average pain score in Herbmed Plus group was 0.45 and average pain score in Herbmed group was 1.15. Average hematuria score in Herbmed Plus group was 0.06 and average hematuria score in Herbmed group was 0.35.

|  | N | Complete clearance | Average duration of clearance | Average pain score | Average hematuria score |
| --- | --- | --- | --- | --- | --- |
| Group Herbmed plus | 108 | 98 (90.7%) | 8.7 weeks | 0.45 | 0.06 |
| Group Herbmed | 54 | 31 (57.4%) | 10.4 weeks | 1.15 | 0.35 |

In exploratory trial on 10 patients of Renal stone for the Capsule of Herbmed plus 500 mg with Gomutra kshar 150 mg given together for twice a day for total 90 day around 6 patients showed a significant reduction in stone size of this treatment group.

Another clinical Trial carried by AMAI Trust ACE Hospital,

"An open label two arm randomized trial to evaluate the safety and efficacy of herbal preparation 'Herbmed plus' in ureteral stent discomfort against anticholinergic"

Stent Dysuria Trial 50 pts were evaluated for stent dysuria by a standard USSQ (ureteral stent symptom questionnaire). Patients were allocated randomly into two groups. One group had received herbal preparation Herbmed plus one capsule after meals twice a day till the ureteral stent was in situ. The other group had received traditional anti cholinergic Tolterodine sustained release tablet 4 mg once a day till the stent was in situ. The patients were evaluated on the basis of USSQ maintained by the patients at home. At the end of analysis, data were as following. 24 patients received Herbmed Plus and 26 pts received Tolterodine Patients were evaluated according to the standard USSQ (ureteral stent symptom questionnaire) which will evaluate the symptoms like dysuria, hematuria, loin pain, suprapubic pain, urgency, urge incontinence and disturbance of routine activities.

| Group | Total no. of patients | Total score | Average score |
| --- | --- | --- | --- |
| H | 24 | 37.55 | 1.56 |
| T | 26 | 102.3 | 3.65 |

| Symptom | H group (no = 24) | T group (no = 26) |
| --- | --- | --- |
| Dysuria | 14 (58.3%) | 26 (100%) |
| Haematuria | 13 (54.1%) | 17 (65.3%) |
| Loin Pain | 17 (70.8%) | 24 (92.3%) |
| Suprapubic pain | 10 (41.6%) | 22 (84.6%) |
| Frequency | 07 (29.1%) | 13 (50%) |
| Urgency | 02 (8.3%) | 09 (34.6%) |
| Urge incontinence | 00 | 00 |
| Disturbance of routine activities | 00 | 01 (3.8%) |
| No of Patients consumed analgesics | 07 (29.1%) | 19 (73.0%) |

| | H group | | T group | |
| --- | --- | --- | --- | --- |
| Symptom | Total score | Avg score | Total score | Avg score |
| Dysuria | 60 | 2.5 | 150 | 7.2 |
| Haematuria | 54 | 2.2 | 98 | 3.6 |
| Loin Pain | 73 | 3.0 | 122 | 5.1 |
| Suprapubic pain | 31 | 1.2 | 82 | 3.7 |
| Urgency | 09 | 0.3 | 27 | 1.5 |
| Urge incontinence | 00 | 0.0 | 00 | 0.0 |
| Disturbance of routine activities | 00 | | 00 | |
| No of tablets consumed | 19 | 0.7 | 85 | 3.1 |

There is clear evidence of increased or enhanced efficacy in these findings that when the active principles, namely Varun, Banana, Yav, Aghada extracts are given as a combination the percentage of patients showing renal clearance was more than the percentage of patients who showed renal clearance after administering varun and banana extracts combination, as in prior art.

Therefore, the efficacy of the combination of active principles of Varun, Banana, Aghada, Yav and Gomutra extracts is more than the additive efficacy of the active principles of Varun and Banana extracts [Patent No. 249299 (Application No. 2128/MUM/2006), granted on Oct. 17, 2011]

Thus, it is seen that the combination of Varun, Banana, Aghada, Yav and Gomutra extracts has better synergistic result in the treatment of kidney stone, renal calculi and other urinary disorders like inflammation and urinary stent related problems.

Clinical Studies II

1. A 48 year male presented with the symptom of abdominal pain. An X-ray examination and USG revealed a kidney stone on the left side of the kidney. The size of the stone was 20×2 mm the patients was given the formulation (500 mg) cap in accordance with this invention, two times a day (one in the morning with breakfast and one in the evening with meals) for a period of one month. After one month of treatment, again the patient underwent an X-ray examination and USG. The surface area was found to be decreased by 22%. The size of the stone after one month of treatment was 15×2 mm 2. A 21 year old male diagnosed with a left renal calculi of size 5×4 underwent the treatment with the formulation (a 500 mg capsule) two times a day (one in the morning with breakfast and one in the evening with meals) for a period of one month. After one month of treatment, again the patient underwent an X-ray examination and USG. The surface area was found to be decreased by 20%. The size of the stone after one month of treatment was 4×4 mm 3. A 61 year old female diagnosed with multiple stones in the right side, of sizes 10×4, 10×4 14×10, 10×4 volunteered for the treatment with the formulation as exemplified herein above. The patients was given the formulation (500 mg) cap in accordance with this invention, two times a day (one in the morning with breakfast and one in the evening with meals) for a period of one month. After one month of treatment, again the patient Underwent an X-ray examination and/USG.

The surface area was found to be decreased by 11%. The sizes of the stone after 1 month of treatment were 10×4, 8×3, 14×10, and 6×2 mm respectively.

4. A 22 year old male presented with symptoms of abdominal pain. Upon examination a 7×3 mm size calculi located on the left side was found. He was given the formulation (500 mg) cap in accordance with this invention, two times a day (one in the morning with breakfast and one in the evening with meals) for a period of one month. After one month of treatment, again the patient underwent an X-ray examination and/or USG. The surface area was found to be decreased by 12%. The sizes of the stone after 1 month of treatment was 6×3 mm 5. Another male aged 47 years diagnosed with a single renal calculi (14×8) on the left side volunteered for the treatment. He was given the formulation (500 mg) cap in accordance with this invention, two times a day (one in the morning with breakfast and one in the evening with meals) for a period of one month. After one month of treatment, again the patient underwent an X-ray examination and/or USG. The calculus was found to be broken into two calculi of sizes 8×4 mm and 5×1 mm Thus there was reduction of 67% in the surface area of the calculi after the treatment duration of one month.

6. A 33 year old female diagnosed with renal calculi of sizes 7×6 and 3×3 on the left side. Underwent the treatment with the formulation (500 mg cap) in accordance with this invention, two times a day (one in the morning with breakfast and one in the evening with meals) for a period of one month. After one month of treatment, again the patient underwent an X-ray examination and/or USG. The size of the stone after 1 month of treatment was 7×5 and 3×3. Thus there was a reduction of 15% in the surface area of the calculi after the treatment duration of one month.

7. A female aged 55 years presented with the symptoms of hematuria was diagnosed for a kidney stone on the right side of size 23×14 mm She was given the formulation (500 mg capsules) in accordance with this invention, two times a day (one in the morning with breakfast and one in the evening with meals) for a period of one month. After one month of treatment, again the patient underwent an X-ray examination and/or USG. The size of the stone after 1 month of treatment was 20×14 mm Thus there was a reduction of 4% in the surface area of the calculi after the treatment duration of one month.

8. A 24 year old male diagnosed with a calculi of size 7×3 on the right side and another one on the left, measuring 9×3 mm, underwent the treatment with formulation (500 mg capsules) in accordance with this invention, two times a day (one in the morning with breakfast and one in the evening with meals) for a period of one month. After one month of treatment, again the patient underwent an X-ray examination and/or USG. It was found that the calculi on the right side were completely dissolved while the size of calculi on the left side was 6×3 mm Thus there was reduction of 62% in the surface area of the calculi after the treatment duration of one month.

9. A 42 year old female diagnosed with multiple small ureteric fragments of sizes 25×3 mm and 17×2 mm underwent the treatment with the formulation (500 mg cap) 2 times a day (one in the morning with breakfast and one in the evening with meals) for a period of one month. After one month of treatment, again the patient underwent an X-ray examination and/or USG. It was found that the ureteric fragments were completely expelled.

10. A 52 year old male presented with symptoms of abdominal pain and hematuria. An X-ray examination revealed calculi of size 25×9 mm He was given the formulation (500 mg cap) 2 times a day (one in the morning with breakfast and one in the evening with meals) for a period of one month. After one month of treatment, again the patient underwent an X-ray examination and/or USG. The size of the stone after 1 month of treatment was 22×9 mm Thus, there was a reduction of 12% in the surface area of the calculi after the treatment duration of one month.

The scientific evidence as described herein above thus shows that the treatment using the combination of Varun, Banana, Aghada, Yav extract (and optionally Gomutra extracts) as prepared in the accordance with this invention reduces the size of the renal calculi. Furthermore, the effect such treatment over a period of time varies from reduction in the size of the calculi to complete expulsions of the calculi which need to be confirmed further studies. Still furthermore, such treatment also took care of the secondary symptoms like inflammation because of its anti-inflammatory effect.

It also helps in reducing pain, heamaturia in inflammatory conditions of urinary system and stent related dysuria.

While considerable emphasis has been placed herein on the specific ingredients of the preferred formulation, it will be appreciated that many further ingredients can be added and that many changes can be made in the preferred formulation without departing form the principle of the invention. These and other changes in the preferred formulation of the invention will be apparent to those skilled in the art from the disclosure herein, whereby it is to be distinctly understood that the foregoing descriptive matter is to be interpreted merely as illustrative of the invention and not as a limitation.

I claim:

1. A herbal composition comprising a dosage form comprising a first composition, comprising:
   a) a powdered mixture of an extract from the bark of *Crataeva nurvala* (Varun bhavit) and an extract of banana stem in an amount of 50%;
   b) an extract from ash of burnt stem, yam and root of *Musa sapientum* (Kadalikshar) in an amount of 15%;
   c) an extract from ash of burnt flowers, leaves, seeds, roofs, and fruits of *Achyranthes aspera* (Apamargkshar) in an amount of 15%; and
   d) an extract from ash of burnt seeds of *Hordeum vulgare* (Yavkshar) in an amount of 20%,
   wherein said percentages of components (a), (b), (c), and (d) are based on the combined weight of components (a), (b), (c), and (d); and
   wherein said dosage form is selected from the group consisting of a tablet and an emulsion.

2. The herbal composition according to claim 1, further comprising a second composition comprising cow urine extract.

3. The herbal composition according to claim 2, wherein said cow urine extract in the second composition is present in an amount of 15-85 wt. % of the total composition.

4. The herbal composition according to claim 3, further comprising at lease one pharmaceutically acceptable additive.

5. The herbal composition according to claim 1, wherein said composition, is administered through oral, nasal, topical, buccal, sublingual, vaginal, parenteral or rectal administration.

6. A method of treating a subject suffering from at least one disorder selected from the group consisting of a kidney stone, inflammation and urinary stent related problems, comprising administering a herbal composition to said patient, said herbal composition comprising a dosage form comparing a first composition, said first composition comprising:
   a) a powdered mixture of an extract from tire bark of *Crataeva nurvala* (Varun bhavit) and an extract of banana stem in an amount of 50%;
   b) an extract from ash of burnt stem, yam and root of *Musa sapientum* (Kadalikshar) in an amount of 15%;
   c) an extract from ash of burnt flowers, leaves, seeds, roots and fruits of *Achyranthes aspera* (Apamargkshar) in an amount of 15%; and
   d) an extract from ash of burnt seeds of *Hordeum vulgare* (Yavkshar) in an amount of 20%,
      wherein said percentages of components (a), (b), (c), and (d) are based on the combined weight of components (a), (b), (c) and (d).

7. The method according to claim 6, wherein said subject is human.

8. The method of treating a subject according to claim 6, wherein said herbal composition is in the form of a capsule, a cachet, a tablet, a powder, a suspension, an emulsion or a paste.

9. The method of treating a subject according to claim 6, wherein said herbal composition is administered through oral, nasal, topical, buccal, sublingual, vaginal, or parenteral or rectal administration.

10. A method of treating a subject suffering from at least one disorder selected from die group consisting of kidney stones, post lithotripsy fragment stones, pre-operative treatment and expulsion of renal calculi, recurrence and reformation of renal calculi, urinary inflammation, and stent dysuria comprising administering a herbal composition to said patient, said herbal composition comprising a dosage form comprising a first composition, said first composition comprising:
   e) a powdered mixture of an extract from the bark of *Crataeva nurvala* (Varun bhavit) and an extract of banana stem in an amount of 50%;
   f) an extract from ash of burnt stem, yam and root of *Musa sapientum* (Kadalikshar) in an amount of 15%;
   g) an extract from ash of burnt flowers, leaves, seeds, roots, and fruits of *Achyranthes aspera* (Apamargkshar) in an amount of 15%; and
   h) an extract from ash of burnt seeds of *Hordeum vulgare* (Yavkshar) in an amount of 20%,
      wherein said percentages of components (a), (b), (c), and (d) ARE BASED ON THE combined weight of components (a), (b), (c), and (d).

11. The method of treating a subject according to claim 10, wherein said subject is human.

12. The method of treating a subject according to claim 10, wherein said herbal composition is administered through oral, nasal, topical buccal, sublingual, vaginal, or parenteral or rectal administration.

13. The method of treating a subject according to claim 10, wherein said herbal composition is in the form of a capsule, a cachet, a tablet, a powder, a suspension, an emulsion or a paste.

* * * * *

UNITED STATES PATENT AND TRADEMARK OFFICE
CERTIFICATE OF CORRECTION

| | | |
|---|---|---|
| PATENT NO. | : 9,259,441 B2 | |
| APPLICATION NO. | : 14/002940 | |
| DATED | : February 16, 2016 | |
| INVENTOR(S) | : Suresh Balkrishna Patankar | |

It is certified that error appears in the above-identified patent and that said Letters Patent is hereby corrected as shown below:

In the Claims

Column 15, line 32, change "die" to --the--;

Column 16, line 19, change "ARE BASED ON THE" to --are based on the--.

Signed and Sealed this
Sixteenth Day of August, 2016

Michelle K. Lee
*Director of the United States Patent and Trademark Office*